United States Patent [19]
Hodosh

[11] 3,936,887
[45] Feb. 10, 1976

[54] ARTIFICIAL IMPLANT AND METHOD OF MAKING SAME

[76] Inventor: Milton Hodosh, 145 Whitmarsh St., Providence, R.I. 02907

[22] Filed: Dec. 10, 1973

[21] Appl. No.: 423,585

[52] U.S. Cl. ................. 3/1; 32/10 A; 128/92 C; 260/42.52; 260/998.11; 264/19; 264/139
[51] Int. Cl.² .. A61C 13/08; A61F 1/00; C08K 3/04
[58] Field of Search ...... 260/42.52, 998.11; 264/29; 3/1; 32/10 A; 128/92 C, 92 CA

[56] References Cited
UNITED STATES PATENTS 2,480,821  9/1949  Connell ........................... 260/42.52
3,786,134  1/1974  Amagi et al. ......................... 264/49

OTHER PUBLICATIONS

Modern Plastics Encyclopedia, 1970–1971, p. 342.

Primary Examiner—James H. Derrington
Attorney, Agent, or Firm—Salter & Michaelson

[57] ABSTRACT

An artificial implant comprising as its essential ingredients vitreous carbon and an acrylic polymer having substantially the characteristics of polymethylmethacrylate, and the method for making same.

6 Claims, No Drawings

ARTIFICIAL IMPLANT AND METHOD OF MAKING SAME

BACKGROUND AND SUMMARY OF THE INVENTION

It is well known in the art to utilize an acrylic polymer, such as one having substantially the characteristics of polymethylmethacrylate, as the base material for an artificial implant. Note, for example, my U.S. Pat. No. 3,609,867, dated Oct. 5, 1971; and also my co-pending applications Ser. No. 60,983, filed July 6, 1970, now U.S. Pat. No. 3,790,507, and Ser. No. 186,442, filed Oct. 4, 1971, now U.S. Pat. No. 3,789,029.

As is known, acrylic polymers, such as polymethylmethacrylate, have many characteristics that make them highly desirable for use as an artificial implant, which characteristics include the fact that this material may be readily molded to any desired shape whereby the implant can be "tailor made" to conform identically to the shape of the anatomical structure that is being replaced. Where used as a tooth implant, this type of plastic material has been found to be desirable, since it closely approaches a natural tooth in hardness and rigidity, is not adversely affected by the temperature conditions normally encountered in the human mouth, and has good retention characteristics with respect to color and composition. Also, the chemical and physical properties of a polymer implant can be altered or modified by combining certain ingredients with the polymer, as exemplified by my aforesaid copending applications Ser. Nos. 60,983 and 186,442.

It has recently been found that vitreous carbon has interesting possibilities as an implant material, and particularly as the root portion for dental implants. Vitreous carbon has the advantage of being a highly inert material, perhaps the most inert material known in implantation procedures, and as such, it is not easily degraded in the oral environment, and produces no obvious adverse reactions within the surrounding tissues. In addition to its chemical inertness, vitreous carbon is light, hard, and has a low coefficient of linear thermal expansion. Also, vitreous carbon unlike metals, is resistant to corrosion at body temperatures and contains no impurities that could become tissue irritants.

On the other hand, vitreous carbon has certain disadvantages insofar as implantation procedures are concerned in that vitreous carbon implants must be preformed by a lengthy process and cannot be readily fabricated; and hence an exact fitting replica cannot be easily constructed, whereby in some cases the jaw structure has to be surgically modified so as to render the carbon implant acceptable. Also, since vitreous carbon is an extremely brittle material, implants made of this material are subject to fracture and breakage. In addition, vitreous carbon is incompatible with metals, and carbon implants therefore cannot easily be processed upon metal strengtheners, but rather metal can only be glued or cemented to effect a connection to a vitreous carbon implant. Another disadvantage is that a vitreous carbon implant appears to form no periodontal-like membrane.

It has now been found, however, as per the present invention, that by combining an acrylic polymer, such as polymethylmethacrylate, with vitreous carbon, in certain proportions and by using certain methodology, a highly desirable artificial implant may be obtained.

It is therefore a primary object of the present invention to provide an artificial implant that is readily formable to any desired shape, that is not adversely affected by normal temperature changes, is relatively hard and strong but is not unduly brittle, and which is highly inert, whereby no adverse reaction takes place within the surrounding tissues.

It is a further object to provide an artificial implant about which forms a periodontal-like membrane that more closely approaches that of a natural tooth.

Still a further object is the provision of an implant of the character described wherein by using a particular form of vitreous carbon a desired degree of porosity is imparted to the composition, thereby resulting in improved connective tissue attachment with the surrounding host.

Another object is the provision of an implant designed to be used as the root portion of an artificial tooth, the composition of the implant being such as to effectively receive and fuse with a polymer crown.

Other objects, features and advantages of the invention will become obvious as the description thereof proceeds.

DESCRIPTION OF THE INVENTION

It has been found that by combining an acrylic polymer, such as polymethylmethacrylate, with vitreous carbon, a highly desirable artificial implant is obtained. As previously stated, such an implant possesses the desirable characteristics of the polymethylmethacrylate, such as ready workability to any desired shape, desirable hardness, rigidity and strength, and desirable insensitivity to normal temperature changes. In addition, the resultant implant possesses certain desirable characteristics which result from the presence of the vitreous carbon in the composition, such as increased chemical inertness, thereby lessening, if not entirely eliminating, any adverse reaction or irritation with surrounding tissues. Also, by utilizing vitreous carbon microballoons in the composition, it has been found that a desired degree of porosity inherently results adjacent the surface of the final composition as a result of the sandblasting step that forms a part of the method of making my implant, as hereinafter described. This porosity contributes to better connective tissue attachment between the implant and the surrounding host. Still another advantage which results from the vitreous carbon polymethylmethacrylate mixture is the fact that the periodontal-like membrane which forms around the implant appears to more closely approach the alignment of the periodontal membrane of a natural tooth.

In making an implant in accordance with the present invention, vitreous carbon, either in powdered form (200 mesh) or in the form of microballoons in the order of approximately 10 to 100 microns, is combined with polymethylmethacrylate, it being understood, however, that the powdered vitreous carbon could be other than 200 mesh and further that other size microballoons could conceivably be used. Samples containing anywhere from ¼ of 1% to 50% vitreous carbon by weight have been mixed with polymethylmethacrylate. To this mixture is added .6 cc of a monomer per gram of the total dry mixture. The mixtures are then mixed and packed into plaster molds, which molds, held in flasks under pressure, are processed at approximately 300° to 500° F. for approximately 30 minutes, after which they are quenched in cold tap water. The molded implant is then removed from the mold and is sandblasted for approximately one minute at approximately 120 P.S.I.G.'s to remove the outer skin which inherently exists thereon.

Where the implant is made from vitreous carbon microballoons, it has been found to possess some degree of porosity adjacent its outer surface as a result of the balloons apparently bursting during the sandblasting operation. On the other hand, implants made from powdered vitreous carbon appear to have no such porosity.

As would be expected, implants containing the least amount of vitreous carbon are stronger and less brittle but possess a somewhat lesser degree of chemical inertness. It is felt that a mixture comprising 97% polymethylmethacrylate and 3% vitreous carbon microballoons results in the best composition for implant purposes, and particularly the root portion of dental implants, since such a composition possesses the desired chemical inertness, and at the same time there is not sufficient vitreous carbon present to make the implant undesirably brittle. As previously stated, the surface porosity that results from the bursting of the vitreous carbon microballoons from sandblasting is desirable, since such porosity promotes better connective tissue attachment with the surrounding host, i.e., surrounding tissues are actually able to infiltrate into the pores of the implant.

SPECIFIC EXAMPLE

Using Cynocephalus baboons, the teeth to be replaced were removed and invested in Plaster of Paris in a flask. When the plaster hardened, the natural teeth were removed from the flask, and a separating media (SS White) was applied to the two halves of the hardened plaster mold. Vitreous carbon microballoons (10 to 100 microns) were mixed with clear polymethylmethacrylate, the mixture comprising 3% by weight vitreous carbon and 97% by weight polymethylmethacrylate. This dry mixture was thoroughly mixed, and a monomer was then added thereto, the amount of monomer being 0.6 cc's per gram of dry mixture. The mixture was again thoroughly stirred and was then packed into the plaster mold, which mold was then held in a flask under pressure and heat processed at approximately 300° F. for approximately 30 minutes. The flasks were quenched in cold tap water, after which the implants were removed and finished down to size and then sandblasted with a fine quartz (Jelenko) at 120 P.S.I.G.'s for approximately one minute to remove the outer skin from the implants. The implants were then washed in running cold tap water for approximately 2 minutes and then implanted into their respective alveoli and splinted into position with autopolymerizing acrylic and stainlesssteel wire. The splints were kept in place for 5 months before removal. At the time of implantation, the implants were well accepted by the baboon's oral tissues. Clinically epithelial attachments were evident, since the gingival sulci were comparable to that which exists about natural dentition. The gingival tone, textue and consistency about the implants were within normal range. After removal of the splints, approximately 5 months after implantation, it was noted that the implants were firmly entrenched. In fact, these implants appeared to progressively sink more deeply into the jaw upon subsequent examination.

Microscopic study of the tissues surrounding the replica tooth implants revealed normal alveolar bone with a cortex outlining and conforming to the shape of the roots of the implant. The cortex was slightly thinner than that in relation to the adjacent natural teeth. The gingiva was somewhat hyperplastic, but the epithelial attachment of the gingiva appeared to attach to the implant at a height comparable to that of the epithelial attachment of the adjacent natural teeth. The gingiva was infiltrated with chronic inflammatory cells, primarily lymphocytes and plasma cells, but scattered polymorphonuclear leukocytes and histiocytes were noted. Between the implant and the alveolar bone of the periodontium, there was a definite periodontal or periimplant membrane. The peri-implant membrane was seen to be composed of dense collagen bundles running from the alveolar bone to the implant and appeared to enter the pores in the implant surface. Hemorrhages were found where the implant had been torn away from the investing peri-implant membrance prior to embedding and sectioning of the tissues.

In certain areas, the peri-implant membrane was highly vascular, and reactive bone could be observed adjacent to the peri-implant connective tissue. One interesting observation was that in many areas of the peri-implant membrane the connective tissue fibers were oriented in a horizontal or diagonal direction. Expressed differently, the fibers appeared to run at right angles to the longitudinal axis of the implant rather than being more parallel to it. This more closely approached the fiber orientation in the natural periodontal membrane of the baboon. In some areas where the peri-implant membrane penetrated into the pores of the implant, there appeared to be some initial calcification.

It is interesting to note that in prior polymer implants the orientation of the collagen fibers of the periimplant (periodontal) membrane was more in a direction generally parallel to the longitudinal axis of the implant, whereas, as indicated above, in the present invention, the collagen fibers extend in a more horizontal or diagonal direction, which more closely approaches the orientation of the periodontal fibers in natural teeth. Although the complete significance of this finding has not as yet been fully explored, it will be obvious that the closer approach to a natural tooth is both beneficial and desirable.

It therefore will be apparent that by combining an acrylic polymer, such as polymethylmethacrylate, with vitreous carbon, it is possible to make an artificial implant of any desired shape within an hour's time, which implant will have all the desirable characteristics of a pure polymer implant, with the added advantages of vitreous carbon, namely, excellent tissue compatability. The percentage of vitreous carbon can be varied in the mixture, depending on the strength of the end product desired; although it has been found that less than one per cent by weight vitreous carbon will not add significantly to the inertness of the mixture, while if more than 50% by weight of vitreous carbon is used, the mixture becomes entirely too brittle. As previously indicated, a mixture of 97% polymethylmethacrylate and 3% vitreous carbon has been found to give optimum results. The vitreous carbon may be in either powder form or in the form of microballoons, although the latter is preferred, particularly for dental implants, since the microballoons create a surface porosity in the end product which enhances fibrous interconnection between the implant and surrounding tissue.

Since the vitreous carbon imparts a dark color to the composition, its use as an implant is limited to the root portion thereof. The presence of polymethylmethacrylate in the composition permits the crown portion of the implant to be much more easily and effectively united with the root portion, in contrast, for example, to the situation where the root portion is solely vitreous carbon. This is particularly true where the crown is a polymer.

It will be understood that the mixture of vitreous carbon and polymethylmethacrylate is effectively applicable to all areas where prior polymer implant materials have been used, including the use of the mixture as a coating for metallic pins or implants. In addition, other materials can be mixed with the vitreous carbon-polymethylmethacrylate composition, such as blowing agents — for example, Dinitrosopentamethylene tetramine — in order to create more porosity in the composition, etc. Also, grated anorganic bone could be added to achieve the benefits stated in copending application Ser. No. 60,983; and N-tributyl phosphate could be added to achieve the benefits disclosed in copending application Ser. No. 186,442. The essential and basic ingredients of the present invention, however, are simply vitreous carbon and polymethylmethacrylate.

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or that form their functional as well as conjointly cooperative equivalents are therefore intended to be embraced by these claims.

What is claimed is:

1. An artificial implant comprising a composition consisting essentially of vitreous carbon and polymethylmethacrylate, said vitreous carbon comprising between ¼ of 1% and 50% of the composition by weight, said vitreous carbon being in the form of microballoons.

2. In the implant of claim 1, said vitreous carbon comprising approximately 3% by weight of the composition.

3. The implant of claim 1 further characterized in that the outer skin of said implant has been removed, whereby the outermost microballoons are bursted.

4. The implaint of claim 2 further characterized in that the outer skin of said implant has been removed, whereby the outermost microballoons are bursted.

5. An artificial implant comprising a composition consisting essentially of powdered vitreous carbon and polymethylmethacrylate, said vitreous carbon comprising between ¼ of 1% and 50% of the composition by weight.

6. In the implaint of claim 5, said vitreous carbon comprising approximately 3% by weight of the composition.

* * * * *